United States Patent
Wang

(10) Patent No.: US 11,426,733 B2
(45) Date of Patent: Aug. 30, 2022

(54) SYSTEM, METHOD AND SAMPLE CARRIER FOR ASSAYING

(71) Applicant: Yantai Ausbio Laboratories Co., Ltd., Shandong (CN)

(72) Inventor: Zhaoqiang Wang, Shandong (CN)

(73) Assignee: Yantai Ausbio Laboratories Co., Ltd.

( * ) Notice: Subject to any disclaimer, the term of this patent is extended or adjusted under 35 U.S.C. 154(b) by 420 days.

(21) Appl. No.: 16/479,205

(22) PCT Filed: Jan. 19, 2017

(86) PCT No.: PCT/CN2017/071718
§ 371 (c)(1),
(2) Date: Jul. 18, 2019

(87) PCT Pub. No.: WO2018/133008
PCT Pub. Date: Jul. 26, 2018

(65) Prior Publication Data
US 2019/0381501 A1 Dec. 19, 2019

(51) Int. Cl.
*B01L 3/00* (2006.01)
*B01J 19/00* (2006.01)
(Continued)

(52) U.S. Cl.
CPC ....... *B01L 3/50853* (2013.01); *B01J 19/0046* (2013.01); *G01N 35/04* (2013.01);
(Continued)

(58) Field of Classification Search
CPC .... B01L 3/0241; B01L 3/0244; B01L 3/0255; B01L 3/0262; B01L 2300/0672;
(Continued)

(56) References Cited

U.S. PATENT DOCUMENTS 5,888,834 A * 3/1999 Ishikawa ............... B01L 3/5085
436/518
6,943,035 B1 * 9/2005 Davies ................. B01J 19/0046
422/502
(Continued)

FOREIGN PATENT DOCUMENTS

EP 1355146 10/2003
FR 2 652 286 3/1991
(Continued)

OTHER PUBLICATIONS

Partial Supplementary European Search Report, dated May 12, 2020, issued for European Patent Application No. 17892147.4, 13 pages.
(Continued)

*Primary Examiner* — Jill A Warden
*Assistant Examiner* — Dwayne K Handy
(74) *Attorney, Agent, or Firm* — Klarquist Sparkman, LLP

(57) ABSTRACT

A sample carrier for assaying can include a plurality of pins having a surface that is capable of picking up at least one substance on the surface. The pins can be arranged such that one or more of the plurality of pins are introduced into a corresponding reaction vessel of a microplate. The sample carrier can be divided into a plurality of modules, with each of the plurality of modules comprising one or more pins of the plurality of pins. Methods of use include placing the sample carrier onto a microplate so that at least the one or more of the plurality of pins extend into the corresponding reaction vessel of the microplate.

5 Claims, 9 Drawing Sheets

(51) Int. Cl.
*G01N 35/04* (2006.01)
*G01N 35/10* (2006.01)

(52) U.S. Cl.
CPC ... *G01N 35/1079* (2013.01); *B01J 2219/0047* (2013.01); *B01J 2219/00317* (2013.01); *B01J 2219/00547* (2013.01); *B01L 2300/021* (2013.01); *B01L 2300/044* (2013.01); *B01L 2300/0672* (2013.01); *B01L 2300/0829* (2013.01); *G01N 2035/0418* (2013.01)

(58) Field of Classification Search
CPC ..... B01L 2219/00317; B01L 2300/044; B01L 2300/0829; B01J 2219/00317; G01N 35/02; G01N 35/028; G01N 35/04; G01N 2035/04; G01N 2035/0403; G01N 2035/0418; G01N 2035/0422
See application file for complete search history.

(56) References Cited

U.S. PATENT DOCUMENTS

| | | | |
|---|---|---|---|
| 2003/0124599 A1 | 7/2003 | Chen et al. | |
| 2004/0018615 A1* | 1/2004 | Garyantes | B01L 3/563 435/305.2 |
| 2004/0089330 A1 | 5/2004 | Muller | |
| 2004/0101966 A1 | 5/2004 | Davis et al. | |
| 2004/0191807 A1 | 9/2004 | Shirazi et al. | |
| 2005/0180892 A1 | 8/2005 | Davies et al. | |
| 2007/0026439 A1 | 2/2007 | Faulstich et al. | |
| 2009/0214811 A1 | 8/2009 | Sandell et al. | |
| 2013/0064739 A1* | 3/2013 | Koskinen | B01L 3/50825 422/554 |
| 2014/0162908 A1* | 6/2014 | Lee | B01L 3/5088 506/39 |
| 2014/0261708 A1 | 9/2014 | Wright et al. | |

FOREIGN PATENT DOCUMENTS

| | | |
|---|---|---|
| JP | S58-127143 A | 7/1983 |
| JP | H08-178926 A | 7/1996 |
| JP | H08-178926 A | 7/1996 |
| JP | H11-001202 A | 1/1999 |
| JP | 2005-187054 A | 7/2005 |
| JP | 2007-003351 A | 1/2007 |
| JP | 2007-017252 A | 1/2007 |
| JP | 2007-532867 A | 11/2007 |
| JP | 2002-505400 A | 2/2022 |
| WO | WO 0060116 | 10/2000 |
| WO | WO 02/20161 A1 | 3/2002 |
| WO | WO 03097239 | 5/2004 |
| WO | WO 2004101153 | 9/2004 |

OTHER PUBLICATIONS

International Search Report and Written Opinion, dated Oct. 9, 2017, for PCT Application No. PCT/CN2017/071718, 8 pages.

* cited by examiner

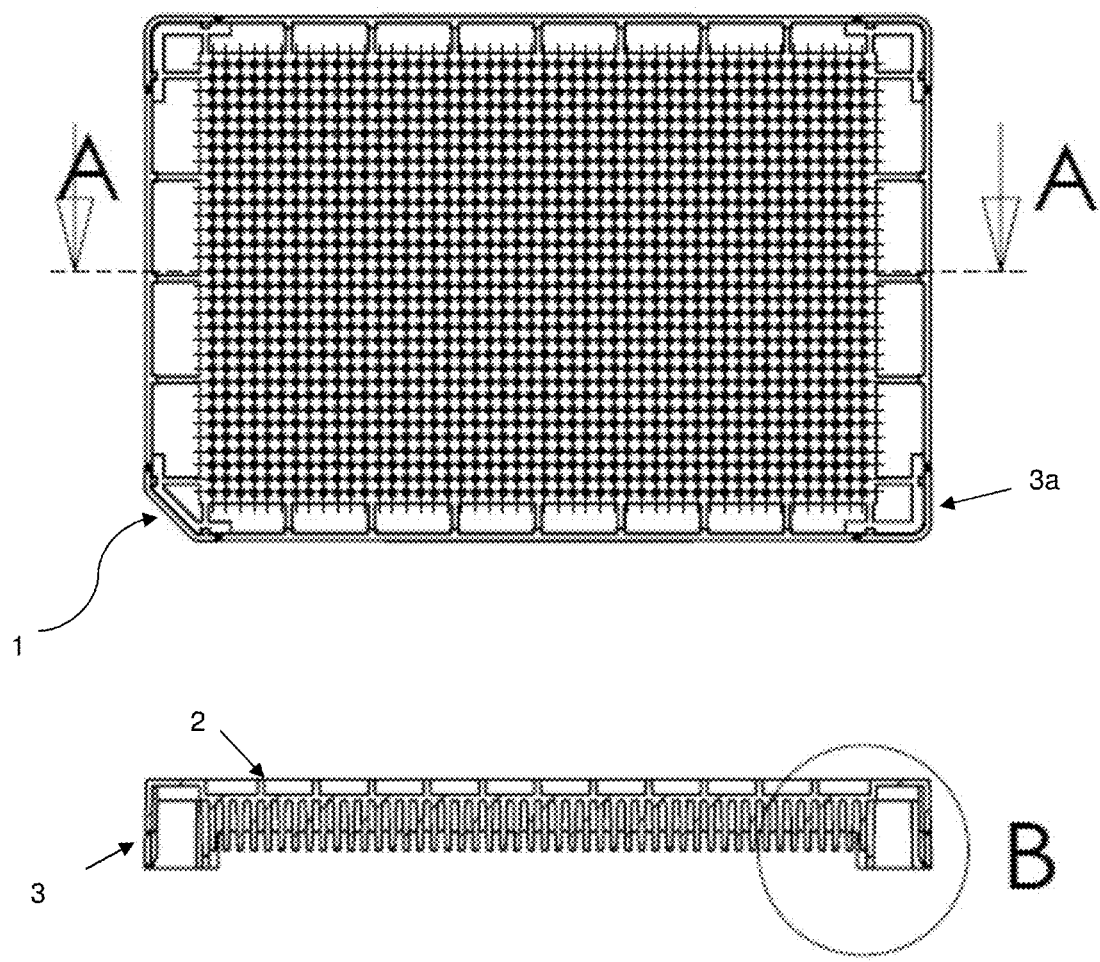
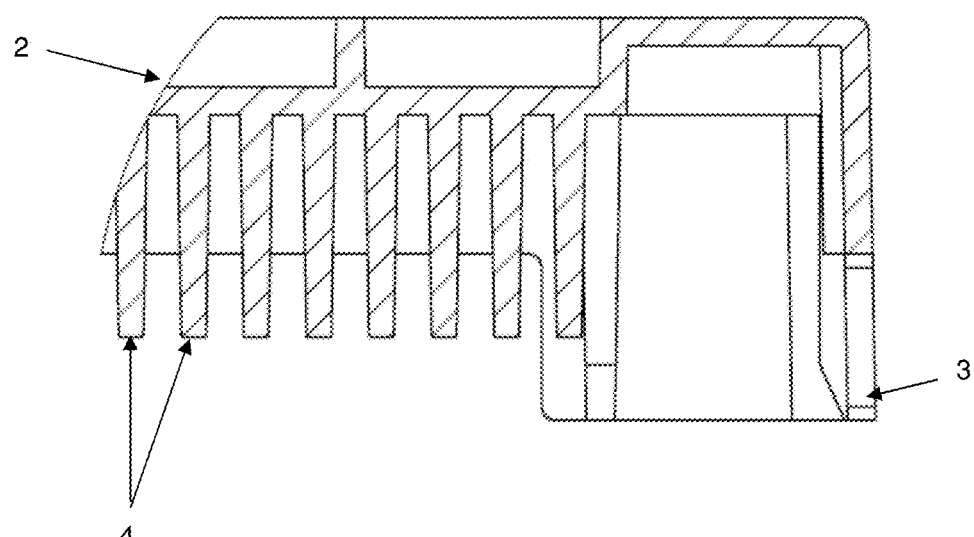
Fig. 1A
Fig. 1B

SYSTEM, METHOD AND SAMPLE CARRIER FOR ASSAYING

CROSS REFERENCE TO RELATED APPLICATION

This is the U.S. National Stage of International Application No. PCT/CN2017/071718, filed Jan. 19, 2017, which was published in English under PCT Article 21(2). International Application No. PCT/CN2017/071718 is incorporated herein by reference in its entirety.

FIELD OF THE INVENTION

The invention relates to a field of biomedical assays. In particular, the invention relates to a sample carrier for assaying, a method for assaying using the sample carrier and a system for assaying.

BACKGROUND OF THE INVENTION

Microplates, also called as Multiwell plates or Microtiter plates are one of the most pivotal disposable labware available. There is a wide range of plate types that have a standardized footprint, supporting equipment and measurement systems.

The early microplates were handmade before Injection molding was developed in the 1960s and served as the manufacturing basis of the commercialized 96-well microplate. Molded acrylic was later replaced with polystyrene (PS), the most common plastic material used in microplates today.

Common usage of the microplate in a laboratory started in the late 1950s, and the immune assays such as enzyme-linked immunosorbent assays (ELISA) were developed in the mid-1970s as a safer and convenient alternative to radioimmunoassay (RIA) before CLIA 2 (Chemiluminescent Immunoassay), the latest generation of assay technology appeared in the early 1990s.

An alternative approach to pathogen detection involves molecular diagnostic technology such as real-time quantitative polymerase chain reaction (RT-qPCR), which enables the detection and quantification of nucleic acids amplification of a specific DNA or RNA sequences.

A singleplex solid phase binding assay is characterized as reaction vessel coated with only one capture probe (e.g. protein such as antibody or antigen), and the sample is added to determine whether any of the single analytes could be detected. An advantage of such parallel singleplex tests is that the subsequent confirmatory/differentiation tests to determine the subtype or stages of the infection is not necessary, and therefore the additional costs associated therewith can be reduced or even eliminated. There is no interference between different type of coated proteins in one well and therefore, maximizes the sensitivity and specificity of the assay.

However, a disadvantage of the separate testing of several analytes is that besides the personnel costs also the material costs will increase substantially. The number of relevant analytes and the varying pattern due to the various pathogen life cycles also makes the detection difficult. Most of the time it is not known at which stage of the infection is. Therefore, it is required that a broad range of various analytes spanning several different stages are tested.

Consequently, the higher the number of analytes to be tested the higher the costs but also, the higher the number of separately performed testing which each by itself and in combination can be regarded as a single test useful for the diagnosis. Conducting more tests with the same or smaller working volumes of patient sample and assays is critical, as increases in volumes and vials directly affect processing costs.

Multiplexing and miniaturization in terms of the size of reaction vessel and working volume are therefore desirable features. Contemporary popular multiplex immunoassays are the art of such, for instance, the Luminex platform, whereby high-affinity capture ligands are immobilized discretely on fluorescent activated plastic micro-beads and mixed with the sample in the liquid phase.

For intended use in blood screening, the specificity must be very high to avoid loss of healthy blood unit due to false positives. The assay must be very sensitive as well, to detect targeted analytes when the pathogen level is low to shorten the window period. Substantial resources have been invested in developing screening and diagnostic techniques with the aim of shortening the time between initial infection and detection of the disease.

For instance, the progression of HCV immunoassays has significantly shortened the window period observed in first-generation assays by an average of 5 weeks and permitted anti-HCV to be detected as early as 10 weeks after exposure. Current improved combination antibody/antigen immunoassays have a window period that is several days longer than that of Nucleic Acid Amplification Test (NAAT). The first-generation HCV assays were based on a yeast-expressed recombinant protein containing only one epitope from the NS4 region (C100-3) of the HCV genome. Second- and third-generation assays used a multiplex format and included antigens from the core, NS3, and NS4 regions; Fourth generation has improved sensitivity and shorten the time between infection with HCV and the appearance of detectable antibodies.

In contrast to singleplex assays, more sensitive and expensive tests, such as recombinant immunoblot (RIBA), Western Blot or nucleic acid tests are often needed to confirm positive screening of multiplex results or to detect a low level of circulating pathogen, and to identify and differentiate the groups and subtypes of the pathogen.

This is problematic, for instance, Hepatitis B virus (HBV) has been classified into eight genotypes, A to H, some of which have been further divided into a number of subgenotypes. Differentiation between HIV-1 and HIV-2 is clinically important. In other cases, multiplex assays ('cocktail' mixture) that screen against several concurrent or co-infected pathogens simultaneously, additional discriminatory protocol are needed to differentiate positive result among the pathogens.

Several manufacturers offer multiplex assays that allow for the simultaneous detection and differentiation. For instance, Bead-based Bio-Plex 2200 HIV Ag/Ab provides separate results for HIV-1 and HIV-2 antibody. However, the multiplex protocol is reframed in a way to have minimum possible deviations from the working protocol of the singleplex assay. The possibility of cross interaction/interference among different molecules is quite likely and may cause undesired results. The vulnerability to cross-reactivity increases quadratically with the number of targets may produce a false positive signal and background noise. It was found the fourth generation HW combination assay has the possibility in open a second diagnostic window due to reduced sensitivity for antibodies. It may occur during a transition period of undetectable levels of both HIV p24 Ag and HIV Ab.

The challenge of additional emerging pathogens of concern is revealed in a list published, which includes viruses like Chikungunya and Dengue as well as bacteria and 34 parasites, mutants of already known viruses that would escape detection using the existing blood donor screening tests and many other non-routine blood-transmissible agents. This poses a unique challenge to the development of multiplex assays, the multiple protein molecules must be immobilized under their individual optimal conditions (i.e. differences in electrical charge and hydrophobicity) and at the same time, all the multiple immobilized protein molecules must interact effectively with all analytes and reagents and even diluents under a common assay condition. Kingsmore and colleagues set the practical limit for multiplexing to 30-50 targets, and indeed, current multiplex assays have not been scaled beyond this limit.

If reagents are altered or additional biomarkers are added, the performance of the assay may be undermined, and the entire optimization process must be repeated. It is costly and labor-intensive when the design of micro arrays and bead-based assays to systematic, combinatorial testing for cross-reactivity. Furthermore, empirical testing and a trial-and-error approach are often the only means for testing several primer pairs, because the interaction of the primer pairs with each other can alter the performance of an individual primer pair over its performance when used alone in a reaction.

A more radical approach to counter above obstacles is to not mix the reagents and samples, and two strategies have been proposed: temporal and spatial separation. Patent WO 2010075632 A1 disclosed a Serial multiplex analyte capture (SMAC) that overcomes cross-reactivity by temporally separating reagents, and sequentially adding beads with cAbs and incubating them separately with the corresponding dAbs.

WO 2013029155 A1 discloses a snap chip assembly for multiplexed microarray with spatial separation of dAb, by delivering each dAb to a single microarray spot with the cognate cAb. This approach may be a microarray of single-plex microscale assays.

These non-standardized formats of systems do not facilitate ease of automation, as assays may be run in multiple steps with reagents being added and washed away or separated at different points. Therefore, it is desirable to accommodate a physically separated testing of several analytes based on 384 and 1536 well microplate. The compression of more tests onto a higher density plate reduces the sample-to-sample distance. As liquid handling is a significant time factor in practice, the total analysis time per sample is reduced significantly. A high overall sensitivity is possible with miniaturization as analyte 7 measurement is always conducted while retaining the highest concentration per unit volume attainable for the given sample, with decreased reaction times due to curtailed diffusion distances.

However, there are seldom commercialized 1536 well microplate automated platform because of plate washing and liquid handling, in general, have been very challenging. In terms of washing, which ensures unspecific substances are washed away, while target molecules are retained. The washing steps have a high impact on throughput, sensitivity, specificity, and cost of the whole process. Conventional washers limit test performance of high-density plates because their residual volume becomes a bigger problem as the size of the well get smaller, allows the background to persist. Consequently, increased time and washing steps are needed, and it becomes even more difficult to avoid well-to-well, needle-to-well contamination.

In terms of liquid handling, high-throughput experiment requires liquid handling throughout the process. The liquid form of various materials must frequently be transferred between vessels of varying sizes and/or dispensed onto substrates of varying types. With current market liquid handling methods, the precision of the sample volume deteriorates as the volume becomes smaller; the smaller volume, the poorer precision, thus leading to a low precision in concentration determination of constituents in the sample.

Additionally, reformatting of various assay diluents is an inevitable hurdle which is time consuming and at serious risk of cross contamination. Typically, these liquid components are packaged in bulk and are not pre-filled or standardized in ready to use format. Practitioners would need to reconstitute the components, the stringent requirement for many changes of buffer and the multiple additions of reagents complicate the automation in higher density plates.

Therefore, a washable, or disposable, sample-handling system running in parallel is usually imposed. In contrast to 96- and 384-well parallel disposition, no single-step 1536-well parallel disposition has been reported yet.

The use of pre-filled reagent compositions in single reaction quantities/dose would be very useful, economical and suitable for automation. But foil seal penetration with high-density plate remains the biggest challenge, due to density populated in small wells.

Therefore, there is a need for an automated system for liquid handling and assaying which overcomes the above-mentioned disadvantages.

SUMMARY OF THE INVENTION

It is desirable in any context to convert assays together with compounds or samples into interpretative information (not simply data) as quickly and as efficiently as possible. Therefore, there exists a need for a simplified method to carry out which is also quick, sensitive, either quantitative or semi-quantitative, reproducible and which can be automated. Furthermore, a need with an objective to screening over the entire duration of the infection and in pre- and post-immunization follow-up—for detecting and differentiating IgMs and total immunoglobulins (total Igs), completely simultaneously, i.e. in a one and only assay receptacle, in the same number of incubations, using a single signal system, and in a one and only signal reading time.

The present invention is not limited to the detection infectious virus listed. It also encompasses the generalization of the system, of the sample carrier and of the methods described below to the detection of infection, and/or the monitoring of diseases for which sample profiling is desirable. An application such as detection of drug resistance or mutants; non-microbiological serum biomarkers, as analytical and diagnostic procedures in medicine and cellular-culture is also foreseeable.

The $1^{st}$ embodiment of the invention is a sample carrier for assaying, comprising a plurality of pins at least partially coated by at least one substance on the surface of the pins, the pins designed such that they are capable of being introduced into a corresponding reaction vessel of a microplate.

The $2^{nd}$ embodiment of the invention is a sample carrier for assaying, comprising one or more pins capable of picking up at least one substance on the surface, the pins being arranged such that one or more or preferably all pins can be introduced into a corresponding reaction vessel of a microplate at the same time when the sample carrier is placed onto the microplate.

The 3rd embodiment of the invention is a sample carrier according $2^{nd}$ embodiment, wherein the sample carrier is a sample carrier according to any one of embodiment 1 or 2.

The $4^{th}$ embodiment of the invention is a sample carrier according to any one of embodiments 1 to 3, wherein the microplate conforms to a standard, preferably to an ANSI standard, more preferably to any one of an ANSI/SLAS 1-2004 through ANSI/SLAS 4-2004 standard.

The $5^{th}$ embodiment of the invention is a sample carrier according to any one of embodiment 2 or 3, wherein the picking up of the substance by the pin is in such a manner that the outer surface of the said pin is at least partially coated with the said substance.

The $6^{th}$ embodiment of the invention is a sample carrier according to any one of embodiment 1 to 5, wherein the pins are made from a synthetic polymer, preferably polystyrene.

The $7^{th}$ embodiment of the invention is a sample carrier according to any one of the preceding embodiments, wherein the sample carrier comprises a rack (2) on which the pins are provided.

The $8^{th}$ embodiment of the invention is a sample carrier according to embodiment 7, wherein the sample carrier is molded as a single unit together with the pins and the rack.

The $9^{th}$ embodiment of the invention is a sample carrier according to any one of embodiments 1 to 7, wherein the sample carrier is divided into one or more modules of preferably substantially quadratic cross-section, each module comprising one or more pins.

The $10^{th}$ embodiment of the invention is a sample carrier of embodiment 9, wherein the sample carrier comprises a rack adapted such that the modules are capable of being releasably and/or interchangebly fixed on to the rack.

The $11^{th}$ embodiment of the invention is a sample carrier of embodiment 10, wherein the modules further comprise a locking means provided at a location such that the module is capable of being locked with the rack by a corresponding locking means provided on the rack.

The $12^{th}$ embodiment of the invention is a sample carrier according to any one of embodiments 10 to 11, wherein the sample carrier is provided with at least one groove on the upper surface to enable handling the module on the rack.

The $13^{th}$ embodiment of the invention is a sample carrier according to embodiment 12, wherein the groove is provided on the surface which is opposite to the surface where the pins are provided.

The $14^{th}$ embodiment of the invention is a sample carrier according to any one of embodiments 1 to 13, wherein the sample carrier has or is capable of having 96, 384 or 1536 pins arranged in a regular pattern.

The $15^{th}$ embodiment of the invention is a sample carrier according to any one of embodiments 1 to 14, wherein the substance is a biochemical substance.

The $16^{th}$ embodiment of the invention is a system, comprising a sample carrier for assaying according to any one of embodiments 1 to 15, and a microplate, wherein the pins of the sample carrier are arranged such that they are capable of being introduced into a corresponding reaction vessel of the microplate when the sample carrier is placed onto the microplate.

The $17^{th}$ embodiment of the invention is a method of coating a substance on to one or more pins of a sample carrier according to any one of embodiments 1 to 15, the method comprising the step of coating at least one pin of the sample carrier (P-plate) by placing, preferably for a predetermined period and in a predetermined ambient temperature, the sample carrier onto a microplate (C-Plate), so that the at least one pin reaches within a corresponding reaction vessel of the microplate (C-plate); wherein the corresponding vessel of the microplate (C-plate) comprises a solution comprising the substance, such that the pin is at least partially covered by the said substance when the sample carrier is placed onto the microplate (C-Plate).

The $18^{th}$ embodiment of the invention is a method of embodiment 17, further comprising the steps of washing the at least one pin of the sample carrier (P-plate) by placing, preferably for a predetermined period and in a predetermined temperature, the sample carrier (P-plate) onto another microplate (C-Plate) so that the at least one pin reaches within a corresponding reaction vessel of the microplate (C-Plate), wherein the microplate (C-Plate) comprises a washing buffer.

The $19^{th}$ embodiment of the invention is a method of embodiment 17 or 18, further comprising the step of incubating, by soaking the at least one pin of the sample carrier (P-plate) by placing, preferably for a predetermined period and in a predetermined incubation temperature, the sample carrier (P-plate) onto another microplate (C-Plate) comprising a blocking buffer with an incubation liquid therein.

The $10^{th}$ embodiment of the invention is a method of embodiments 18 or 19, further comprising the step of drying the at least one pin of the sample carrier (1, P-plate) by placing the sample carrier (P-plate) onto a waste plate (W-Plate); and centrifuging, preferably for a predetermined period of time, the assembly of the sample carrier and the waste plate together, to transfer residual buffer on the at least one pin to the corresponding vessels of waste plate (W-Plate).

The $21^{st}$ embodiment of the invention is a method according to any of embodiments 17 to 20, wherein the microplate (13, C-Plate) is characterized in that it is a microplate with either 96, 384 or 1536 reaction vessels arranged in a regular pattern and corresponding to the pins on the sample carrier (P-plate), at least some which vessels contain a liquid; and/or, when the method depends from embodiment 20, the waste plate (W-Plate) is characterized in that it is an empty microplate with either 96, 384 or 1536 reaction vessels arranged in a regular pattern and corresponding to the pins on the sample carrier (P-plate).

The $22^{nd}$ embodiment of the invention is a method of assaying, comprising the step of placing a sample carrier (P-plate) as defined in any one of embodiments 1, 2 or 4, or any one of embodiments 5 to 15, when depending from embodiment 1, onto a microplate (C-plate), preferably for a predetermined time and at a predetermined temperature to incubate, so that at least one, preferably all of the pins reach within a corresponding reaction vessel of the microplate, wherein at least one, preferably all of the corresponding vessels of the microplate (C-plate) comprise a preferably predetermined volume of sample such that the at least one, preferably all pins are at least partially covered by the said sample when the sample carrier (P-plate) is placed onto the microplate (C-plate).

The $23^{rd}$ embodiment of the invention is a method of embodiment 22, wherein the method further comprises the step of incubating, preferably at a predetermined temperature and for a predetermined time, by soaking the at least one, preferably all pins of the sample carrier within the corresponding reaction vessel of another microplate (C-plate), wherein this other microplate (C-plate) comprises a preferably predetermined volume of buffer liquid such that the at least one, preferably all pins are at least partially covered by the said buffer liquid when the sample carrier (P-plate) is placed onto the other microplate (C-plate).

The 24$^{th}$ embodiment of the invention is a method of embodiments 22 or 23, wherein the method further comprises the step of washing the at least one, preferably all pins of the sample carrier (P-plate) by placing, preferably for a predetermined period, the sample carrier (P-plate) onto another microplate (C-plate) so that the at least one, preferably all pins reach within a corresponding reaction vessel of the another microplate (C-plate), wherein the microplate (C-plate) comprises a preferably predetermined volume of washing buffer.

The 25$^{th}$ embodiment of the invention is a method of embodiment 24, wherein the method of washing further comprises, centrifuging the sample carrier (P-plate) together with a waste plate (W-plate) placed such that residual liquid is transferred from the at least one, preferably all pins of the sample carrier (P-plate) to the corresponding vessels of waste plate (W-plate).

The 26$^{th}$ embodiment of the invention is a method according to any of embodiments 22 to 25, further comprising the steps of removing the sample carrier plate (P-plate) from the said microplate (C-plate); and assaying, by measuring the relative light units of each of the corresponding reaction vessels of the microplate (C-plate).

The 27$^{th}$ embodiment of the invention is a method according to any of embodiments 22 to 26, wherein the microplate (C-plate) is a microplate with either 96, 384 or 1536 reaction vessels arranged in a regular pattern and corresponding to the pins on the sample carrier (P-plate), at least some of which contain a liquid.

The 28$^{th}$ embodiment of the invention is a method according to any of embodiments 22 to 26, wherein the microplate is preferably pre-sealed with a pierceable foil to maintain the liquid within the reaction vessels of the microplate (C-Plate).

The 29$^{th}$ embodiment of the invention is a method according to embodiment 28, wherein the method further comprises the step of: prior to placing the sample carrier (P-plate) onto the microplate (C-plate), piercing through the pierceable foil of the microplate (C-plate), wherein the piercing is performed by means of a piercing plate comprising one or more piercing pins corresponding to the reaction vessels of the microplate (C-plate) and capable of piercing through the pierceable foil.

The 30$^{th}$ embodiment of the invention is a method according to embodiment 29, wherein the piercing plate is a puncture module, preferably as defined in any of embodiments 32 to 37.

The 31$^{st}$ embodiment of the invention is a method according to any of embodiments 24 to 30, wherein the third sample carrier (W-plate) is characterized in that it is an empty microplate with either 96, 384 or 1536 reaction vessels arranged in a regular pattern and corresponding to the pins on the sample carrier.

The 32$^{nd}$ embodiment of the invention is a puncture module for piercing a pierceable foil from a sample carrier (C-plate), preferably as defined in embodiment 29, the puncture module comprising: a longitudinal housing, a loading tray capable of supporting the sample carrier (C-plate) and a piercing plate having one or more piercing pins, which can be moved along a predetermined direction into the longitudinal housing of the puncture module, and a plurality of rods provided in parallel to each other in the housing and rotatable along the longitudinal axis of the rods, wherein each of the plurality of rods can be positioned variably in height in relation to each other and in relation to the said loading tray such that when the microplate (C-plate) and the piercing plate are arranged such that the piercing pins of the piercing plate are aligned with reaction vessels of the microplate (C-Plate), the rods are capable of being in contact with the piercing plate.

The 33$^{rd}$ embodiment of the invention is a puncture module of embodiment 32, wherein the plurality of rods are arranged substantially perpendicular to the said predetermined direction.

The 34$^{th}$ embodiment of the invention is a puncture module of embodiment 32 or 33, wherein each of the plurality of rods are displaced at a distance from each other along the said predetermined direction, wherein the distance is a minimum of at least half the length of a microplate (13, C-Plate and a maximum of full length of microplate (13, C-Plate).

The 35$^{th}$ embodiment of the invention is a puncture module of any of embodiments 32 to 34, wherein the height of the rods with respect to the loading tray varies from high to low along the predetermined direction.

The 36$^{th}$ embodiment of the invention is a puncture module of any of embodiments 32 to 35, wherein the loading tray can be moved along the predetermined direction with the help of an electrical motor.

The 37$^{th}$ embodiment of the invention is a puncture module of any of embodiments 32 to 36, wherein the one or more piercing pins of the piercing plate (P-plate) each correspond to a reaction vessel of the sample carrier and are capable of piercing through the pierceable foil.

The 38$^{th}$ embodiment of the invention is a system for assaying comprising, at least one mechanical arm capable of handling a sample carrier as in any of embodiments 1 to 15, a puncture module as in any of embodiments 32 to 37, and a controller configured such that it enables the mechanical arm to handle the sample carrier and perform the method as in embodiment 22.

The 39$^{th}$ embodiment of the invention is a system of embodiment 38, further comprising an incubator unit connected with the controller, wherein the controller is further configured to enable performing the method as in embodiment 23.

The 40$^{th}$ embodiment of the invention is a system of embodiment 38 or 39, further comprising a centrifuge unit connected with the controller, wherein the controller is further configured to enable the system for assaying to perform the method as in embodiment 24.

The 41$^{st}$ embodiment of the invention is a system of any one of embodiments 38 to 40, wherein the controller is further configured to enable the system for assaying to perform the steps as in embodiments 29 and 30.

The 42$^{nd}$ embodiment of the invention is a system of any one of embodiments 38 to 41, further comprising at least one pipetting robot, capable of handling sample reformatting and pre-treatment of the second sample carrier as in embodiment 22.

The 43$^{rd}$ embodiment of the invention is a system of any one of embodiments 38 to 42, further comprising a reader module for reading a barcode and/or a QR-code of a sample carrier (P-plate) as in any of the embodiments 1 to 15.

BRIEF DESCRIPTION OF THE DRAWINGS

FIG. 1A shows a bottom-view and a side-view of a sample Pin-plate according to an embodiment of the invention.

FIG. 1B shows an enlarged section of the pins on the sample carrier.

DESCRIPTION OF THE INVENTION

Figure 2A:
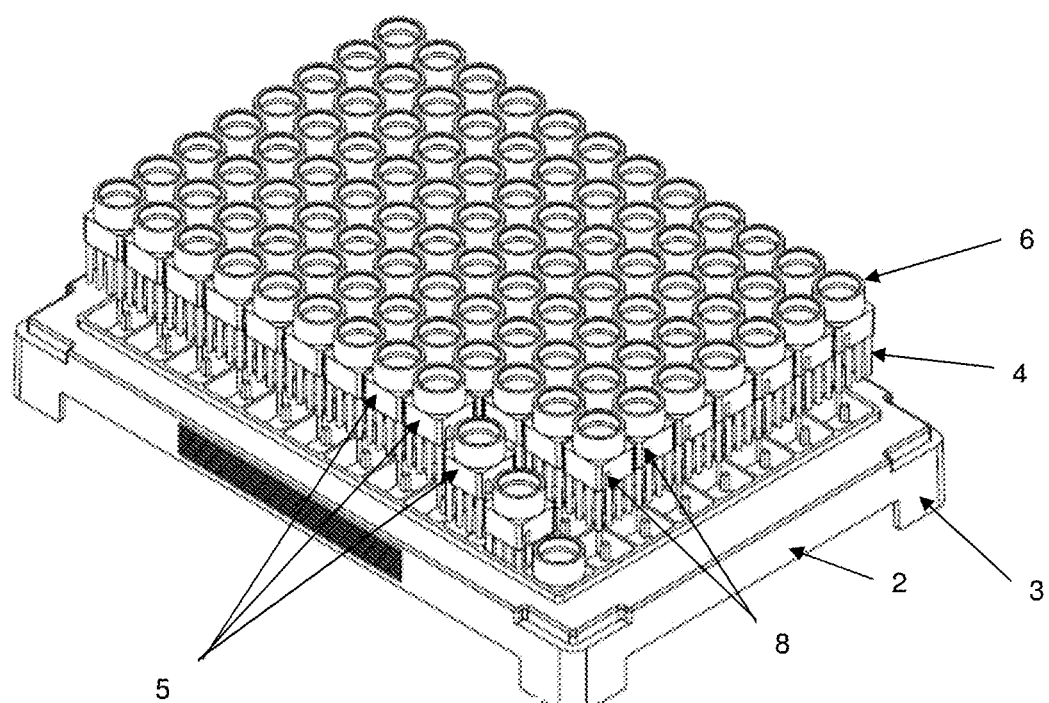
FIG. 2A shows an expanded view of the modular Pin-Plate with interchange module.

FIGS. 1 A and B shows a bottom view and a front view of a sample carrier according to one embodiment of the invention having a plurality of pins (4) formed on one of the surfaces of the sample carrier. The number of pins on the sample carrier can be variable, however, it is designed in line with the technical standards. For example, in the above illustration, the sample carrier is provided with 1536 pins. Other commonly used number of pins are 96 or 384, however, other numbers of pins may also be envisaged and implemented on the sample plate. The pins are provided at an equidistance from each other and evenly distributed along the surface of the sample carrier. The sample carrier (1) is embodied as a rack (2), wherein the pins (4) are arranged in a pattern in accordance with the arrangement of the reaction vessels of a 96 or 384 or 1536 well microplate conform to a standard, such as an ANSI standard. However, such a design is also possible where the pins are unevenly placed along the surface depending on the assay required. For example, a sample carrier 1 having 1536 pins can also be used for a 384-well C-plate, whereby four pins are positioned in one reaction vessel of the C-Plate. Each pin is shaped in a substantially conical shape with a base being in contact with the sample carrier. However, other shapes of the pins such as a cuboid or parallelepiped are also perceived which may provide an enhanced surface coherence. For example, a square, rectangular, triangle, elliptical, round, or multisided-shaped pin, or a combinations thereof may also be envisaged.

As it will be explained below, the shape and size of the pins are designed in accordance with the shape of a corresponding reaction vessel of a Container-plate (C-Plate). Taking into consideration the standard size of a 1536-well C-Plate and the number of reaction vessels, the length of each pin is about 8 mm. A skilled person will understand that for a vessel having a higher depth, the length of the pin may be higher. The shape and size of the pins may also be considered based on the volume of coated substance that is desired, for example on the surface area of the pin. That is, the surface area of the pin is such that the pin is capable of being coated with a desired volume of substance. According to an embodiment, for a sample carrier having 1536 pins, the dimension of each pin may be about 8 mm in height, 0.89 mm in width at the bottom, and 1.17 mm in width at the top. According to another embodiment, for a sample carrier having 384 pins, the dimension of each pin may be about 13 mm in height, 2.72 mm in width at the bottom, and 3.15 mm in width at the top.

The pins on the sample carrier are provided such that they are capable of being coated with a substance on the surface. For this reason, it is preferable that the pins are made from a material having high adherence capability to various substances in order to provide a good surface coherence. On the other hand, it is also preferable to consider the material which is robust and allows easier manufacturing process due to the small size of the pins. It was found that the material such as polystyrene was a suitable material for such manufacturing, however it is also possible that other types of materials are used for manufacturing of the pins such as polyvinylalcohol, polyethyleneglycol, polyvinylchloride, polyetherketon, etc.

The design of the rack (2) as, for example, with a skirt (3) is in a way allowing an easy stacking of the sample carriers as well as an easy and stable placing of the sample carrier 1 on another sample carrier with corresponding skirt (3a) on the top surface of the sample carrier. The design of the rack is also so that the plate confirms to the overall standard for the easy handling of the plates with the existing assay systems. For example, the dimensions of the plate along with the rack is such that it conforms to an ANSI standard, such as for example an ANSI/SLAS standard. Preferably, the sample carrier and the pins are formed as one piece by a molding process using plastic. That is, the rack 2 and the pins 4 are produced as one piece.

Figure 2B:
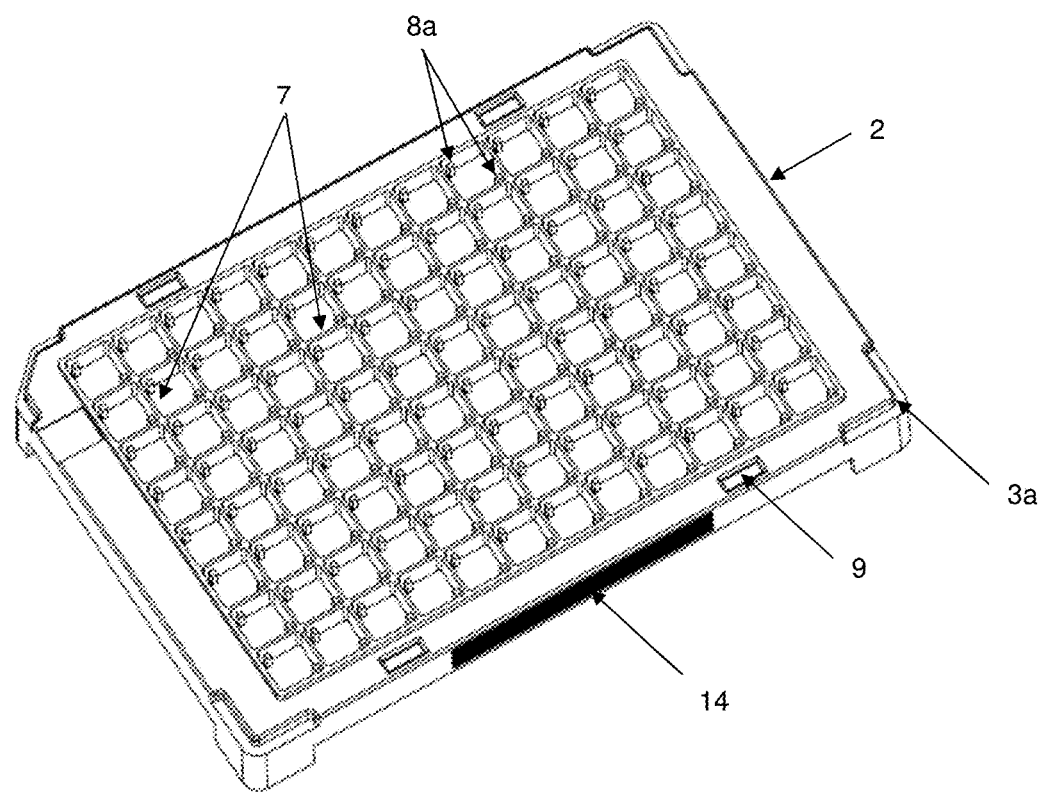
FIG. 2B shows a rack of the modular Pin-Plate according to an embodiment of the invention.

In another embodiment of the invention, one or more pins are produced as a module mountable on the rack as shown in FIG. 2A to 2D. The sample carrier (1) as shown in FIG. 2A shows a plurality of modules (5) each being mounted on the rack (2). In the embodiment of the figure, 96 modules are provided where each module have 16 pins, thereby a total of 1536 pins on the sample carrier. Each module, also called as pin modules are provided with a trajectory (8). As shown in FIG. 2B, the rack is provided with multiple ribs (7) across the surface of the rack to divide the rack into multiple segregated portions capable of accommodating the pin modules. The ribs are provided with guiding slots (8a) along the side surface in the internal side of each segregated portions corresponding to a guiding trajectory (8) on each pin module. The guiding slots (8a) and the corresponding guiding trajectory (8) enable the precise alignment of the modules on the rack.

Furthermore, the guiding slots (8a) and the trajectories (8) are positioned asymmetrically, which ensures that the pin modular are inserted in a predetermined direction to avoid incorrect placement or orientation on the rack.

The modularized Pin-Plate further has a groove (6) on the surface of the top orifice to enables the handling of the modules and the P-plate with a robotic arm. For example, the groove can be a circular groove which is compatible with an Automated Liquid Handling system such as Hamilton's CORE Technology.

Figure 2C:
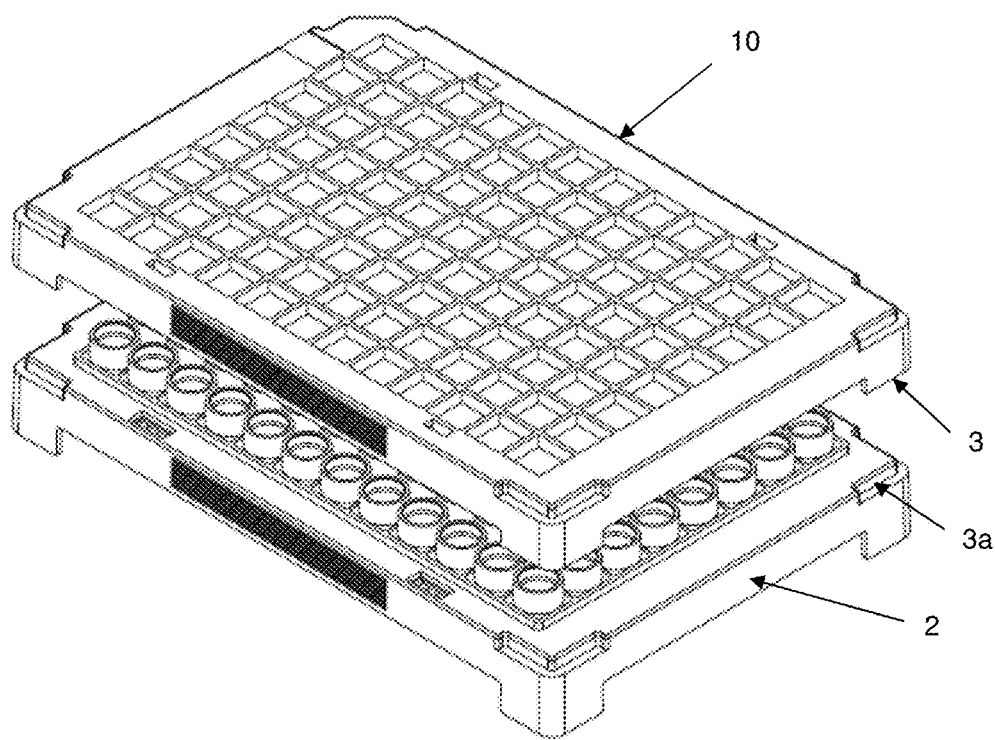
FIGS. 2C and 2D shows an expanded view and a side view of a modular Pin-Plate according to another embodiment of the invention.
Figure 2D:
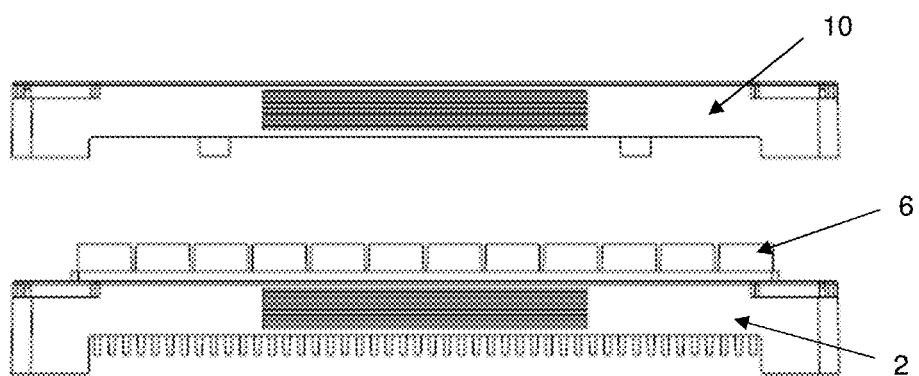

As shown in FIGS. 2C and 2D, the modular pin plate is preferably further provided with an additional plate lid (1o) dimensioned to the shape of the rack such that the rack is capable of being covered over the modular pin surface of the lid. The skirt (3) on plate lid (1o) corresponds with the skirt (3a) on the rack to ensure that all the pin modules are at a unified position on the plate rack and prevents it from being moved. The solid lid is capable of being fastened by use of locking hooks (9a) to fasten together with the corresponding locking hooks (9) on the plate rack in order to prevent unnecessary exposure and pin movement when the entire plate is in motion. Furthermore, a grip (14) is provided on the side surface of the lid plate for handling the lid. Additionally, a label may be adhered or printed on the plate for identification. The identification labels such as barcodes and/or RFID labels may be used or printed on the plate, preferably on the outer surface, an upper-side or a skirt-side of the plate.

Figure 3A:
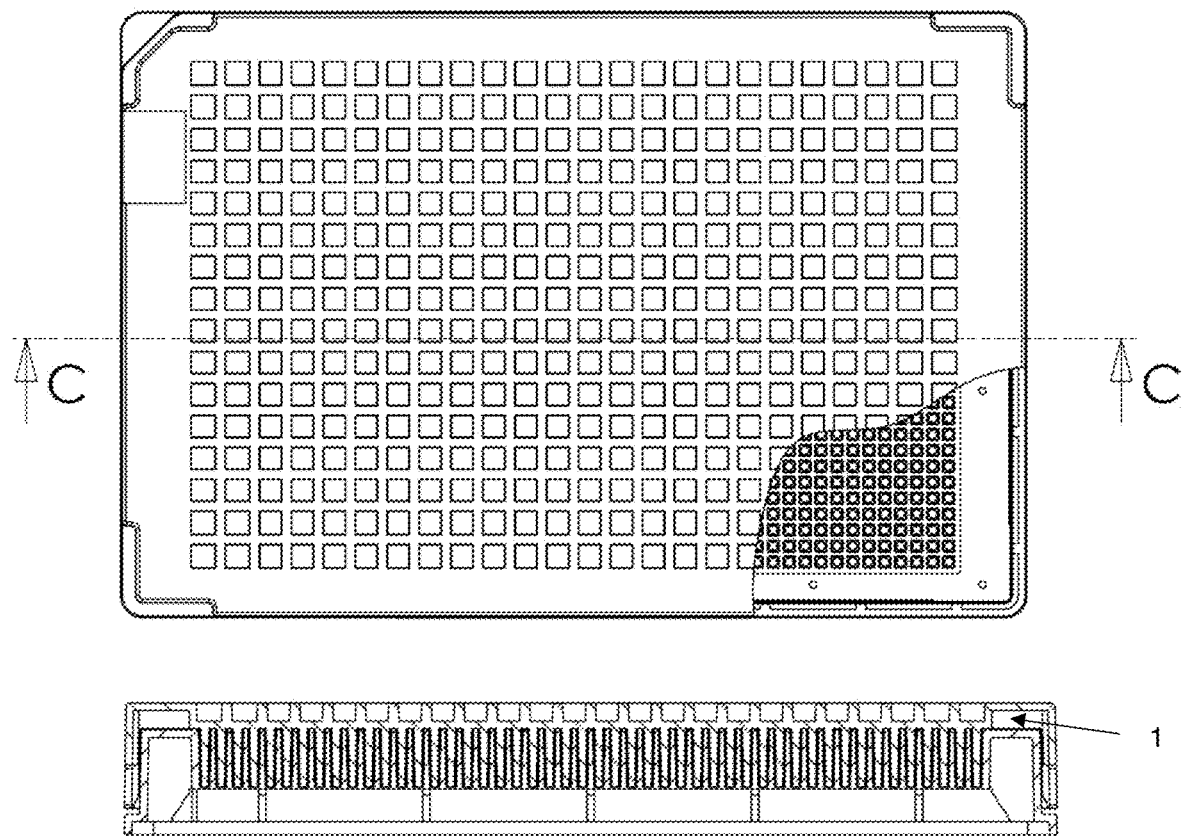
FIG. 3A shows a top-view and a side-view of the sample Pin-plate when introduced into a Container-Plate.
Figure 3B:
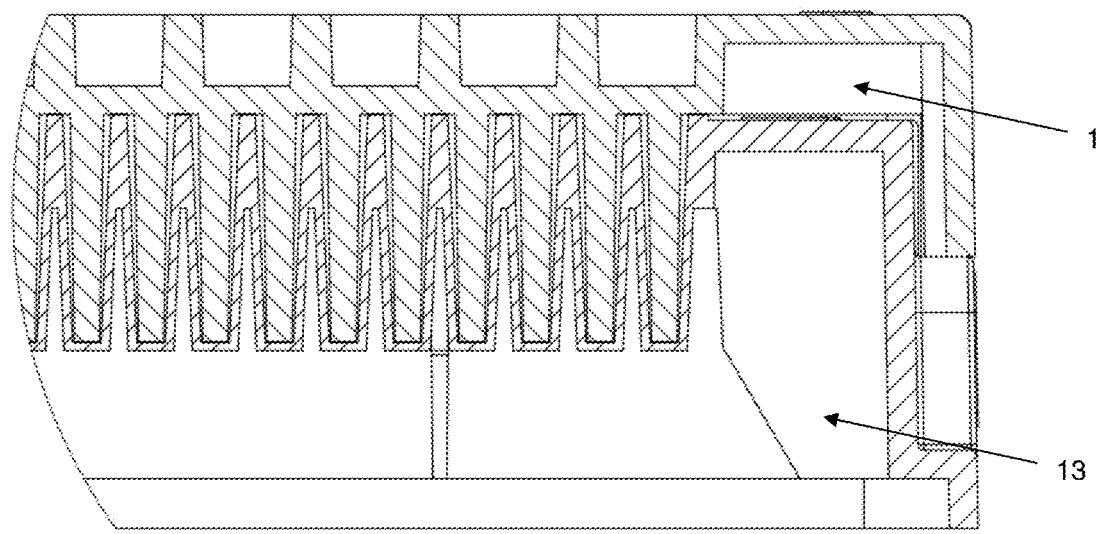
FIG. 3B shows an enlarged section sample Pin-plate when introduced into a Container-Plate.

FIGS. 3A and 3B shows a sample carrier container plate (C-plate) according to an embodiment of the invention when the sample carrier Pin-plate (P-plate) is introduced in the container plate. As shown in the figure, the pins of the sample carrier (P-plate) is introduced into a corresponding reaction vessel of the sample carrier container plate (C-plate) such that the complete pin is in the reaction vessel.

Figure 4:
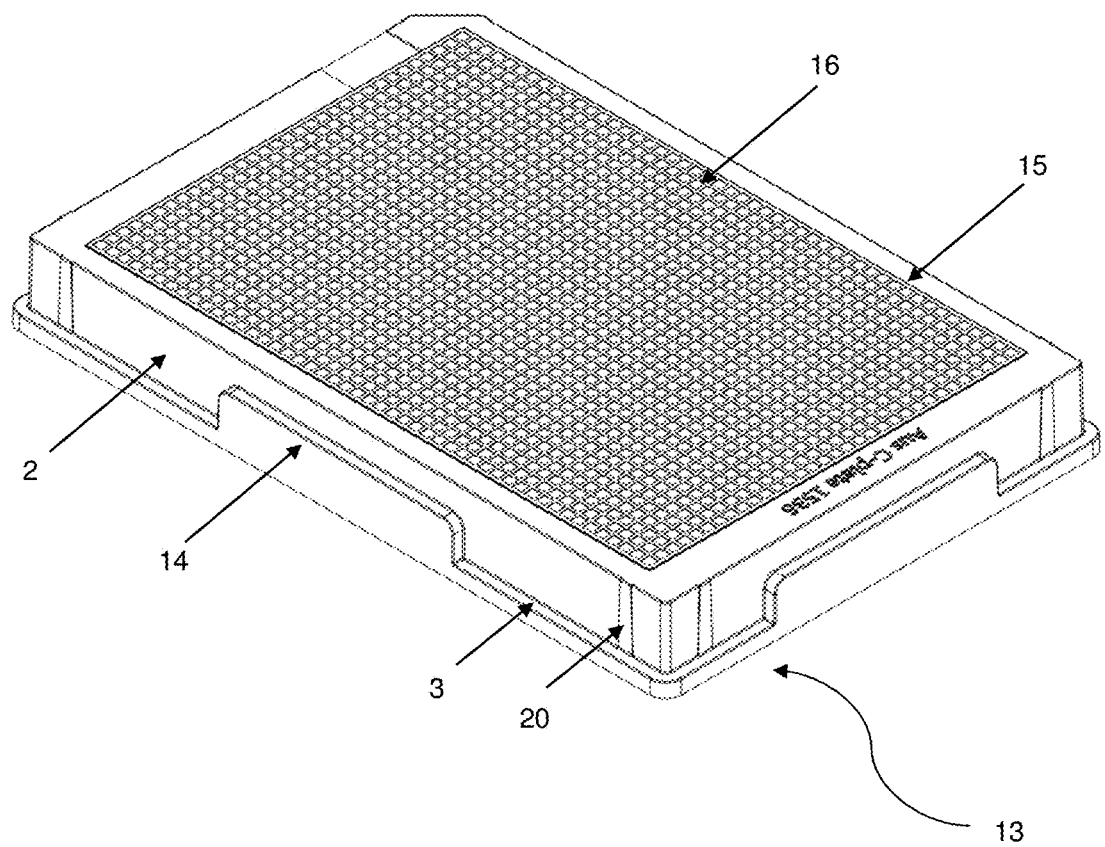
FIG. 4 shows a top view of a container plate sample carrier according to an embodiment of the invention.

The container plate (13) is shown in FIG. 4 contains reagents which reacts with the coated substance on the pin of the pin-plate when the pin is introduced into the reaction vessel. The container plate sample carrier (13) comprising 1536 reaction vessels (16) with a top opening. The container plate (C-plate) sample carrier (13) can be embodied as a rack (2) having a skirt (3) that allowing a stable and easy placement of the sample carrier container plate (13) on either a same kind of sample carrier for stacking, or for example, for placing the sample carrier 13 on another sample carrier Pin plate (1). The container plate may confirm to the overall standard for the easy handling of the plates with the existing assay systems. For example, the dimensions of the container plate are such that it conforms to an ANSI standard, such as for example an ANSI/SLAS standard.

Since the container plate (13) is provided with reagents, in order to avoid contamination or evaporation and also for maintaining the ease of transport and storage, reaction vessels are sealed with a pierceable sealing foil 15 which is liquid impermeable. The pierceable sealing foil 15 can be one selected from the group of aluminum foil, polyurethane foil, polyethylene foil, etc. Preferably, the sealing foil 15 is an aluminum foil.

Figure 5A:
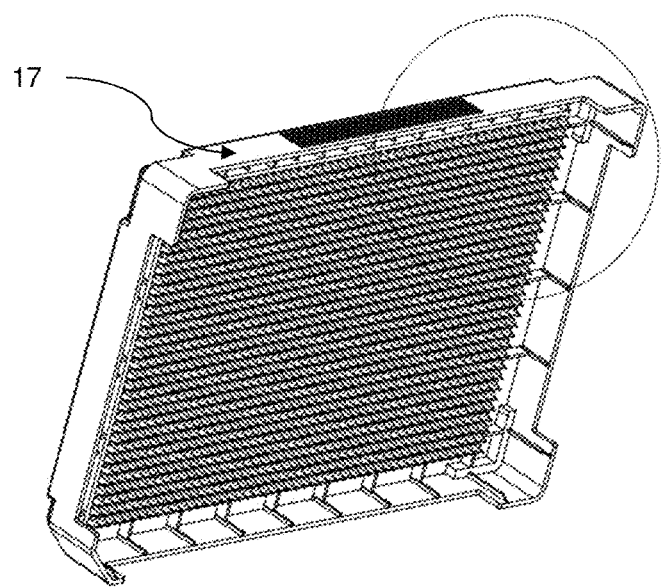
FIG. 5A shows a piercing plate according to an embodiment of the invention.
Figure 5B:
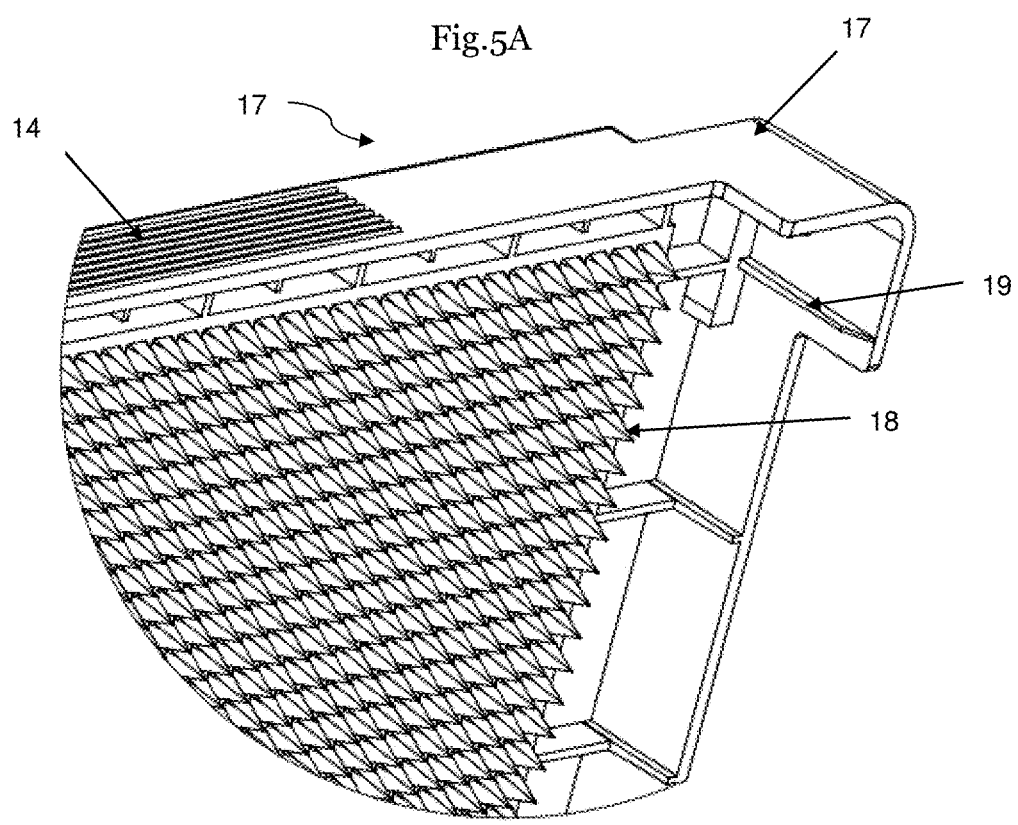
FIG. 5B shows an enlarged view of a piercing plate according to an embodiment of the invention.

To pierce the sealing foil 15 a piercing device 17 can be used as depicted in FIGS. 5 A and B. The piercing device comprises as many piercing needles 18 as reaction vessels 16 are supposed to be pierced. The piercing device 17 with the piercing needles 18 can either be produced as one piece, for example, by plastic molding or the piercing needles 18 can be mounted to the piercing device 17. As shown in the figure, the piercing device 17 can be a rack 2, where the piercing needles 18 are arranged in a pattern in accordance with the arrangement of the reaction vessels 16 needed to be pierced.

The piercing needle 18 according to the present invention can be any kind of needle-type device suitable for piercing sealed sample carriers. Such piercing needles 18 can be any pointed devices that allow a piercing of the foil 15. The piercing needles are designed such that the piercing can be performed without the requirement of a high external force. The structure of the piercing needles can be a spiral-, screw- or cross-shaped for an enhanced piercing effect. When piercing the foil 15 a removal of the foil where attached to the sample carrier should be avoided since this could lead to undesired effects, like cross-contamination, loss of liquid, etc. Hence, the piercing needle 18 should be designed in a way to be sharp enough to easily pierce the foil 15.

Those skilled in the art will know or will be able to adjust the piercing device 17 in an appropriate manner in dependence of the type of foil 15 used in order to achieve a precise and clean piercing of the foil 15 without any undesired side effects.

In order to obtain that the piercing needles precisely align with the reaction vessels 16 to be pierced positioning means like, for example, a guiding pin 19 or a guiding trajectory can be comprised by the piercing device 17.

Figure 6:
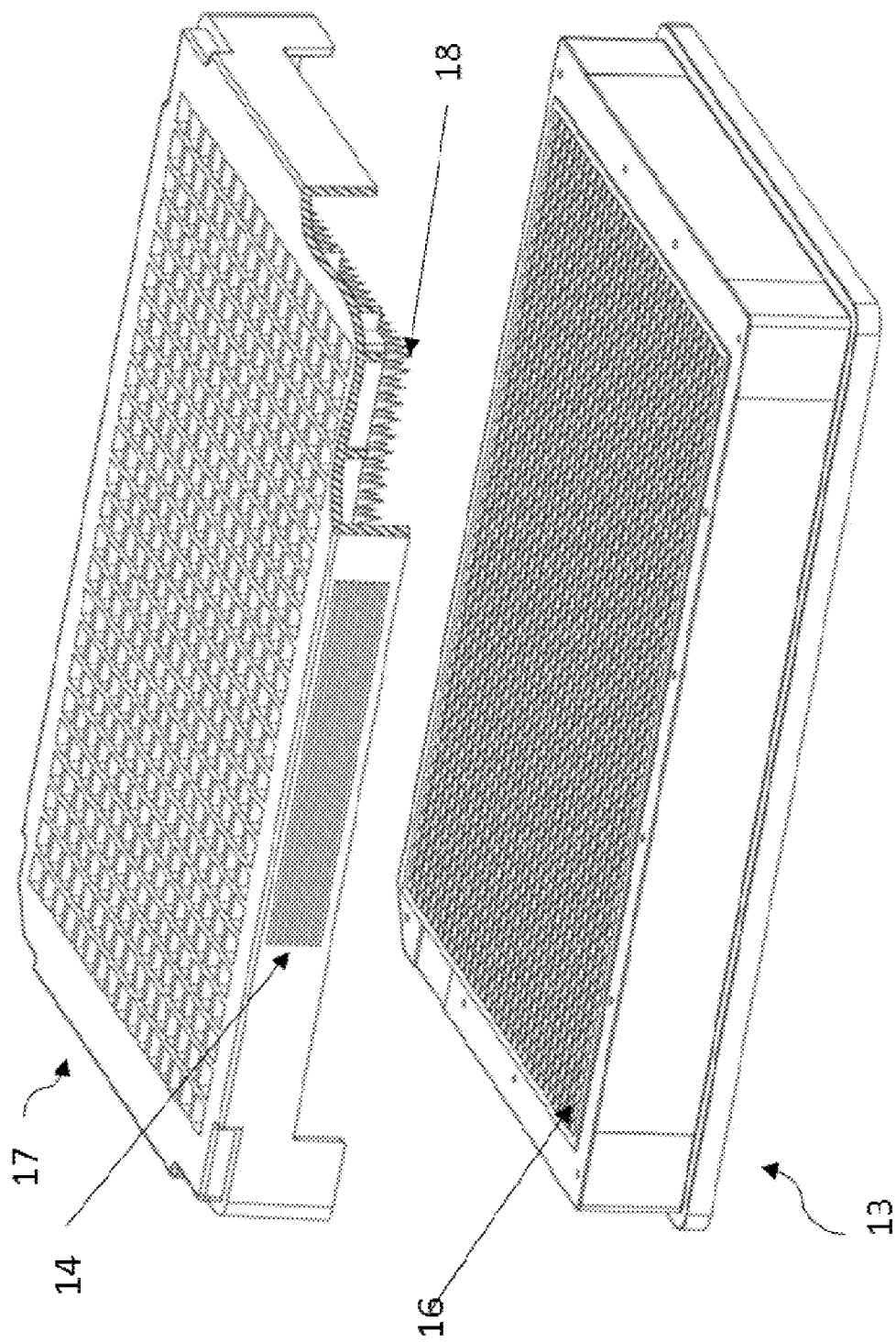
FIG. 6 shows the introduction of piercing plate on the container plate.

FIG. 6 shows the placement of a piercing device 17 onto a container plate sample carrier 13, whereby the piercing needles 18 precisely align with the reaction vessels having an opening 16 of the sample carrier 13. To obtain a stable and rigid assembly of the piercing device 17 and the sample carrier 13 a corresponding guiding pins 19 and guiding trajectories or guiding pins 20 are used. The reaction vessels 16 of the sample carrier 13 are sealed with a pierceable sealing foil 15. By placing the piercing device 17 onto the sample carrier 13 the piercing needles 18 will pierce the foil 15 from the top of the reaction vessels.

However, when using a high-density plate such as 384 and 1536 wells, it is difficult to perform puncture because the wells are very small and densely populated thereby causing a large number of points of penetration. Even more challenging to process the whole plate at once due to the number of wells. Such piercing may be done by a stand-alone pneumatic piercing instrument. However, the instrument requires washing and cleaning procedure to prevent contamination and due to its large size, it is often difficult to be integrated with an automated liquid handling platform.

Figure 7A:
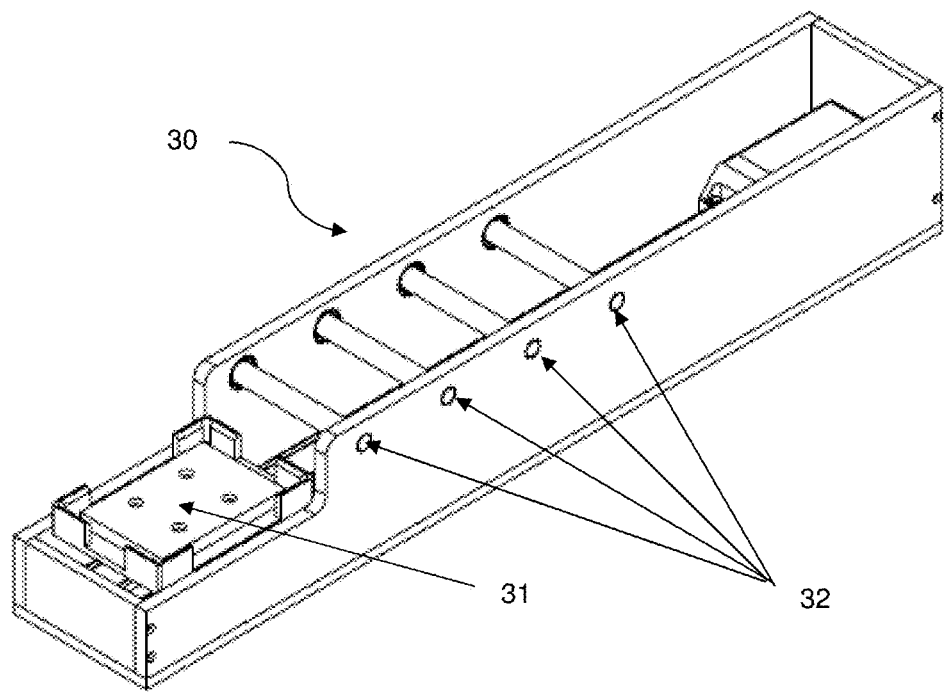
FIGS. 7 A and B shows a puncture module according to an embodiment of the invention.
Figure 7B:
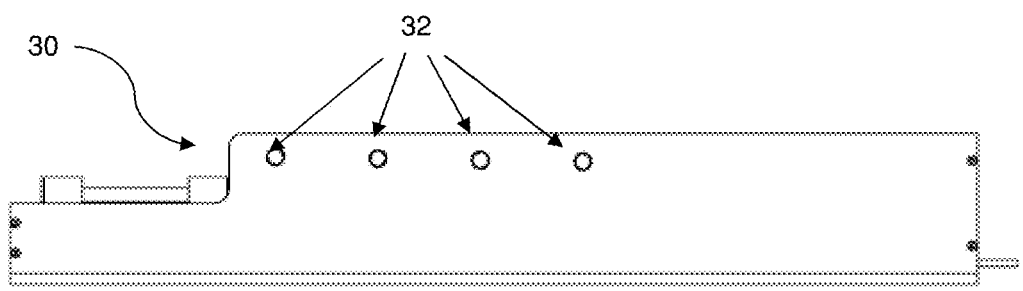

FIGS. 7A and 7B shows a piercing module or pressing module or puncture module (30) according to an embodiment of the invention which is easy to operate and can also be integrated with the automated liquid handling platform. This module is designed to press the piercing plate towards the container plate to puncture the sealing.

The puncture module is a longitudinally shaped module in a horizontal direction which contains a loading tray (31) capable of supporting the sample carrier. The loading tray (31) is also moved along a predetermined direction, that is from the outside towards the inside of the puncture module. This movement of the loading tray (31) is supported by a motor, for example, however, it can also be moved manually along a railing in the vertical direction. The loading tray is also provided with slated grip along the corners to enable easy pick-up and placement of the plate on the loading tray.

Along the longitudinal direction of the puncture module, a plurality of rods (32) are provided in parallel to each other and they are freely rotatable along the longitudinal axis. These rods are positioned at a variable height from each other and from the said loading tray such that when the container plate sample carrier and a piercing plate are placed together as seen in FIG. 6 on the loading tray and moved towards the rods, the rods are in contact with a piercing plate and press them in the downward direction. The rods does not press the entire plate at the same time but instead each row of puncture pins are pressed towards the foil one at a time. Therefore, the pressure required is lesser than that required if all the puncture pins are inserted.

The height of the rods from the loading tray decreases as it moves in the longitudinal direction. This ensures the rods to exert a higher pressure on the piercing plate in a stepped format, thereby pressing the piercing plate into the container plate. The distance between the two rods is approximately the length of the loading tray such that even pressure is exerted by the rods at a single time.

Method of Coating of the Sample Carrier (P-Plate)

The process of coating the P-plate according to the invention with the different substance is described hereinafter.

In a solid-phase immunoassay, the binding between an antigen and its specific antibody takes place at the boundary of a liquid and a solid phase. One of the reactants receptors is immobilized on a surface. The other reactant ligand is initially free in solution. Reactions at the solid-liquid interface can be diffusion limited due to depletion of reactants close to the surface. This effect depends on geometry, intrinsic reaction rate and surface concentration of receptor molecules. For macromolecules reacting at the solid-liquid interface, there will be new diffusion restrictions due to cooperativity among the immobilized receptors and macroscopic distances to overcome before reaction. Consider a well with certain height filled with the ligand solution. The receptor is immobilized at the surface of the well. Since the motion of the ligand molecules in a horizontal direction has no influence on the reaction kinetics, the problem is essentially one-dimensional. The time for diffusion is determined by the equation:

Diffusion time=$X^2/D_{dif}$

X=Diffusion distance to working surface
$D_{dif}$=Diffusion coefficient

The Pin-Plate according to the present invention has the advantage of three-dimensional interfaces of just like coated magnetic beads (microsphere). Moreover, the Pin-Plate of the present invention overcomes the problem of lost beads in washing, which would yield an inconsistent result.

The coating of the P-plate with one or more different substances is performed at the manufacturer's site and the coated P-plate is then provided for performing the assay. However, it is possible that such a coating is also performed at a third party location.

The process of coating includes the steps of placing the Pin-plate on a Container-plate (C-Plate) and allow for incubation for a certain period and at a certain temperature to allow for coating and diffusion. The process is repeated by a washing and/or a drying step as necessary for the coating to be effective.

In the present example, a 1536 pin plate is coated with a different substance for a 16-plexs CLIA for HW, HBV, HCV and TP screening.

Coating: Immense every pin of 1536 sample carrier 1 into a 1536 container plate (C-plate) which consists of 16 different protein coating buffers (5 µl/well). Each well contains only one type of protein buffer, no mixture. For example, the different protein coating buffer are provided for each of the 16 different pins as shown below. This ensures that the different modules are capable of being coated in a similar order of the pins.

Coated proteins corresponding to their coating on the 1536 Pin-Plate (sample carrier 1)

| HIV | gp41 recombinant | gp36 recombinant | p24 recombinant | anti-p24 Monoclonal antibody |
| HCV | NS3-NS4 | NS5 | anti-core Monoclonal antibody | core |
| HBV | HBsAg recombinant | HBcAg recombinant | HBsAb D Monoclonal antibody | HBsAb M Monoclonal antibody |
| TP | TP15 recombinant | TP17 recombinant | TP47 recombinant | TP44.5 recombinant |

The immersed plates are then set to be incubated at 2 to 8 degrees overnight.

Next, the step of washing is performed to wash the extra substance off the pins. For this process, immense 1536 sample carrier 1 into a 1536-well C-Plate with washing buffer (7 µl/well).

The drying of the plate can be performed by using a centrifugal program. For example, place the sample carrier 1 on top of an empty W-Plate into a centrifuge with pins orientate away from the centrifuge axis, then initiate centrifugation program at 100 g for 15 seconds.

Next, the step of blocking is performed. For this process, immense 1536 sample carrier 1 into a 1536-well C-Plate with blocking buffer (6 µl/well) and let it incubate overnight at a temperature of between 2 to 8 degrees.

For NAT coating, additional step of conjugating SA-Biotin probes is needed, for this process, immense 1536 sample carrier 1 into a 1536-well C-Plate with conjugate buffer (5 µl/well), each well contains a single probe, a total of 16 specific probes are added for this example. Then incubate at 37 degrees for 30-60 minutes. Repeat the washing step if necessary.

| HIV | HIV pol | HIV gag | HIV 5'LTR | HIV 3'LTR |
| HCV | HCV 5'UTR | HCV Core | HCV 3'X-tail | HCV 3'UTR |
| HBV | HBV preS2 | HBV ccc | HBV X-gene | HBV preCore |
| TP | polA | TpN47 | tmp | arp |

Finally, the process of drying is performed which is to remove the residual blocking buffer by centrifugation. For this, place the sample carrier 1 on top of an empty W-Plate into a centrifuge with pins orientate away from the centrifuge axis. The centrifugation program is then initiated, for example at 1000 RPM for 1-2 minutes.

Method of Assaying-CLIA

The next step includes the process of assaying using the said coated P-Plate according to the present invention. The method of assaying uses the steps of placing the coated P-plate on a C-plate having the sample to be tested. The method includes repeated steps of incubating along with the step of washing before the sample reading is made.

For CLIA test, the first step involves the step of sample reformatting and pretreatment. Here, using 8 channel pipetting head to aliquot 96 samples from sample tubes (including Positive/Negative QC) into a 96 DWP which contains sample diluent-blocking and nuclease for proteins. Incubate 15 minutes at 37 degrees.

Transfer 5 µl/well of the 96 DWP to a 1536 C-Plate by automated liquid handling platform with 96 channels pipetting head.

Next, the sample is then subjected to incubation by immersing the coated 16plex sample carrier 1 into the 1536 C-Plate, with 1 pin per well. The incubation is performed at a temperature of 37 degrees for a period of 15 minutes.

Next, the residual liquid is removed by placing the sample carrier 1 onto an empty W-Plate, and initiate centrifugation at 150 g for 15 seconds.

Next, the sample carrier is subjected to washing by immerse the sample carrier 1 in a C-plate with washing buffer (7 µl/well). Then a preferable method of drying by placing the sample carrier 1 onto an empty W-Plate, and initiate centrifugation at 150 G for 15 seconds. The cycle is repeated for a necessary number of times, each time with a new washing buffer C-Plate and W-Plate.

Next, the step of biotinylation by immersing the sample carrier 1 in a 1536 C-plate (consist of biotinylated protein conjugate, 5 µl/well). This is subjected to incubation at a temperature of 37 degrees for a period of 7 minutes. The washing step is repeated again if necessary.

Next, the sample carrier 1 is immersed in a 1536 C-plate (consist of SA-HRP, 5 µl/well). This is subjected to incubation at a temperature of 37 degrees for a period of 7 minutes. The washing step is repeated again if necessary.

Next, the sample carrier 1 is immersed in a 1536 C-plate (consist of luminol substrate, 5 µl/well). This is subjected to incubation at room temperature for a period of 2-3 minutes. In our case, luminol is used as a substrate that exhibits chemiluminescence.

Finally, the plate reading is made by remove the sample carrier 1 and read the luminol plate with reference wavelength 425 nm for making the final reading of the assay results.

Method of Assaying-NAT

The next step includes the process of assaying using the said coated P-Plate according to the present invention. The method of assaying uses the steps of placing the coated P-plate on a C-plate having the sample to be tested. The method includes repeated steps of incubating along with the step of washing before the sample reading is made.

For NAT test, the first step involves the step of sample reformatting and lysis pretreatment. Here, using 8 channels pipetting head to format 100 µl of a sample from 96 sample tubes to a 96 DWP which contains lysis buffer with oil overlay. The pipetting channel will first penetrate the oil overlay before engaging in dispensing; then centrifuge the 96 DWP for 2 minutes to make sure sealable oil layer is at the uppermost surface. Then incubate at 60 degrees in thermocycler for 10 minutes.

Next, transfer lysed sample from the 96 DWP to a 1536 C-Plate (pre-filled with hybridization buffer, 2 µl/well) by liquid handling system such as Hamilton S.T.A.R with 96 channels pipetting head, so that each of the 1536 wells contains 50 of the lysed sample. Then centrifuge the C-Plate at 200 g for 2 minutes.

Next, the C-plate is subjected to incubation, transfer the C-Plate to a thermocycler, incubate at 95 degrees for 5 minutes.

Next, quickly insert the Pin-plate (coated with SA and conjugated specific biotin-probes) in the C-Plate. Incubate at room temperature for 20 minutes.

Next, the Pin-plate is subjected to washing, first place Pin-plate on an empty W-plate, then place in centrifuge spin dry at 200 g for 1 minute with the pin orientated away from the centrifuge axis. Then soak the pins in another 1536 C-Plate with washing buffer. Repeat the drying step if necessary.

Next, the P-plate is subjected to amplification. Insert the P-Plate in a reading plate with pre-filled one-step RT-PCR mix, transfer the assembly in thermocycler for 10 minutes in 45 degrees, followed by 5 minutes at 95 degrees. Then repeat 40 times: 95 degrees (5 seconds) followed by 60 degrees (10 seconds) followed by 72 degrees (5 seconds).

Reaction mix composition: 2× SensiFAST™ SYBR No-ROX One-Step Mix, 10 uM Forward Primer, 10 uM Reverse Primer, Reverse transcriptase, RiboSafe RNase Inhibitor, DEPC-H2O.

Lastly, after amplification, place the assembly at room temperature for 20 minutes, then remove the Pin-Plate, and place the reading plate in a fluorescent reader.

Automated Liquid Handling System

Figure 8:
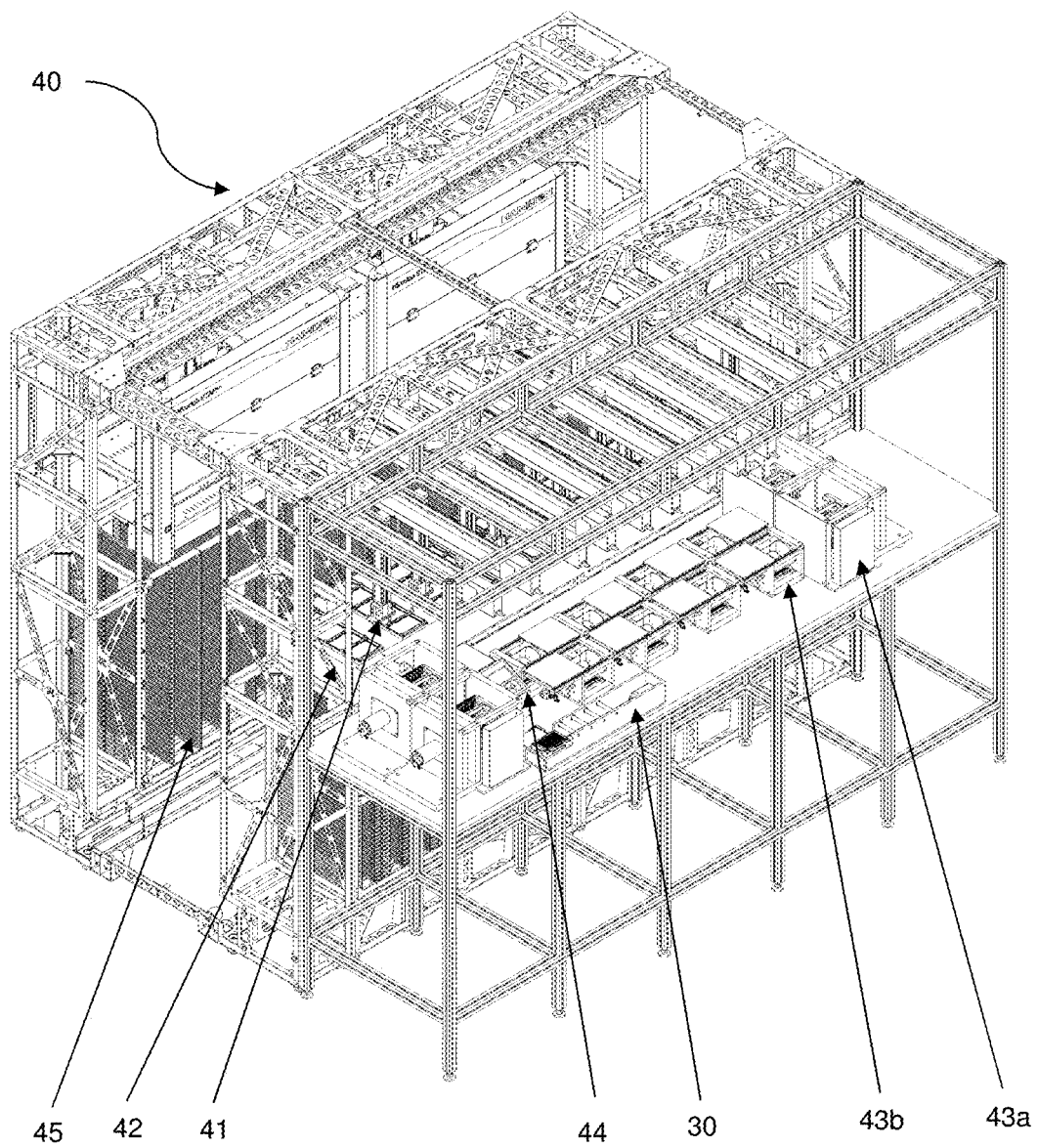
FIG. 8 shows an automated system for assaying.

FIG. 8 shows an overall view of an automated system of assaying according to an embodiment of the invention. The different aspects and embodiments of the present invention as described herein can also be combined, e.g., in a fully automated process including a handling platform.

The liquid handling system may be configured to work along with an existing handling system such as the Automated Liquid Handling system by Hamilton Bonaduz AG.

The system of the invention contains one or more mechanical arm capable of handing the sample carrier plates as described above. In particular, the grip (14) provided on the Pin-plate (1), Container plate (13) and the piercing plate (17) can be gripped by the mechanical robotic arm (41) and the different processes performed.

The system contains pipetting channels, which enables the sample reformatting.

The system also contained the puncture module (30) connected together with the mechanical arm (41) such that arm handles the plates loaded on the loading tray and also operates the movement of the loading tray. Additionally, an electric motor may be used to control the loading tray and assist the mechanical arm in loading and moving the plates and the loading tray.

The system includes a processor, either a standalone microprocessor or a computer connected to the mechanical robotic arm and the other components such as the incubator (42), tube centrifuge (43a), plate centrifuge (43b), plate reader (44), reagent reservoir, plate shaker, plate label reader, plate storage unit (45) which performs the method of assaying without the need for human interference.

In particular, the controller is connected with the incubator such that it can control the incubator by setting the incubation parameters automatically depending on the requirements or on user input control and operating the incubator as configured.

The invention claimed is:

1. A puncture module for piercing a pierceable foil on a microplate, the puncture module comprising:
   a longitudinal housing;
   a loading tray capable of supporting the microplate and a piercing plate having one or more piercing pins, which can be moved along a predetermined direction into the longitudinal housing of the puncture module, and
   a plurality of rods provided in parallel to each other in the longitudinal housing and rotatable along a longitudinal axis of the rods,
   wherein each of the plurality of rods is positioned variably in height in relation to each other and in relation to the said loading tray such that the height of the rods from the loading tray decreases along the predetermined direction into the longitudinal direction, and such that when the microplate and the piercing plate are arranged such that the piercing pins of the piercing plate are aligned with reaction vessels of the microplate, the rods are in contact with the piercing plate.

2. A method of piercing performed by a piercing plate in a puncture module, the method comprising:
   receiving a microplate having a plurality of reaction vessels covered by a pierceable foil and the piercing plate on a loading tray capable of supporting the sample carrier and the piercing plate,
   moving the microplate and piercing plate along a predetermined direction into a longitudinal housing of a puncture module,
   wherein the puncture module comprises a plurality of rods provided in parallel to each other in the longitudinal housing and rotatable along a longitudinal axis of the rods, and
   wherein each of the plurality of rods are positioned variably in height in relation to each other and in relation to the loading tray such that when the microplate and the piercing plate are arranged with the piercing pins of the piercing plate aligned with respective ones of the reaction vessels of the microplate, the rods contact the piercing plate to cause the pierceable foil to be pierced.

3. The method of claim 2, wherein the plurality of rods are arranged substantially perpendicular to the said predetermined direction, and/or displaced at a distance from each other along the predetermined direction, wherein the distance is a minimum of at least half a length of a microplate.

4. The method of claim 2, wherein the height of the rods with respect to the loading tray varies from a higher height to a lower height along the predetermined direction, and wherein the sample carrier and piercing plate are moved along the predetermined direction by an electrical motor.

5. A system for assaying comprising, a sample carrier comprising a plurality of pins having a surface that is capable of picking up at least one substance on the surface, wherein the pins are arranged such that one or more of the plurality of pins can be introduced into a corresponding reaction vessel of a microplate, and wherein the sample carrier is divided into a plurality of modules, each of the plurality of modules comprising one or more pins of the plurality of pins;

at least one mechanical arm capable of handling a sample carrier, the at least one mechanical arm being configured to move the sample carrier onto a microplate;

a puncture module for piercing a pierceable foil of the sample carrier the puncture module comprising a longitudinal housing, a loading tray capable of supporting the sample carrier and a piercing plate having one or more piercing pins, which can be moved along a predetermined direction into the longitudinal housing of the puncture module, and a plurality of rods provided in parallel to each other in the housing and rotatable along the longitudinal axis of the rods, wherein each of the plurality of rods can be positioned variably in height in relation to each other and in relation to the said loading tray such that when the microplate and the piercing plate are arranged such that the piercing pins of the piercing plate are aligned with reaction vessels of the microplate, the rods are in contact with the piercing plate.

* * * * *